United States Patent
Breznock

(10) Patent No.: US 6,863,677 B2
(45) Date of Patent: Mar. 8, 2005

(54) METHOD AND APPARATUS FOR TREPHINATING BODY VESSELS AND HOLLOW ORGAN WALLS

(76) Inventor: Eugene Michael Breznock, 27956 State Hwy. 128, Winters, CA (US) 95694

(*) Notice: Subject to any disclaimer, the term of this patent is extended or adjusted under 35 U.S.C. 154(b) by 0 days.

(21) Appl. No.: 09/938,428

(22) Filed: Aug. 23, 2001

(65) Prior Publication Data

US 2003/0040765 A1 Feb. 27, 2003

(51) Int. Cl.[7] ............................................. A61B 17/32
(52) U.S. Cl. ..................................... 606/184; 606/180
(58) Field of Search ........................... 606/1, 152, 153, 606/170, 184, 185, 167, 180, 181, 182

(56) References Cited

U.S. PATENT DOCUMENTS

| | | | |
|---|---|---|---|
| 3,949,747 A | | 4/1976 | Hevesy |
| 4,018,228 A | | 4/1977 | Goosen |
| 4,122,855 A | | 10/1978 | Tezel |
| 4,191,191 A | * | 3/1980 | Auburn .................. 604/164.06 |
| 4,216,776 A | | 8/1980 | Downie et al. |
| 5,129,913 A | | 7/1992 | Ruppert |
| 5,314,435 A | * | 5/1994 | Green et al. .............. 227/175.1 |
| 5,695,581 A | * | 12/1997 | Lacy ........................ 156/128.1 |
| 5,827,316 A | * | 10/1998 | Young et al. ................ 606/185 |
| 5,868,711 A | * | 2/1999 | Kramer et al. ............... 604/136 |
| 5,893,369 A | * | 4/1999 | LeMole ........................ 606/184 |
| 5,899,122 A | * | 5/1999 | Court ............................ 81/3.2 |
| 5,910,153 A | | 6/1999 | Mayenberger |
| 5,972,014 A | | 10/1999 | Nevins |
| 6,080,173 A | | 6/2000 | Williamson, IV et al. |
| 6,080,176 A | | 6/2000 | Young |
| 6,171,319 B1 | | 1/2001 | Nobles et al. |
| 6,176,867 B1 | | 1/2001 | Wright |
| 6,187,022 B1 | | 2/2001 | Alexander, Jr. et al. |
| 6,394,893 B1 | * | 5/2002 | Scholz et al. ................... 460/6 |
| 6,401,707 B1 | * | 6/2002 | Fladgard et al. ......... 125/16.01 |
| 6,402,252 B1 | * | 6/2002 | Dickson .................... 299/39.6 |

* cited by examiner

Primary Examiner—David O. Reip
Assistant Examiner—Paul A Roberts

(57) ABSTRACT

A system is disclosed for creating a hole in a body vessel or hollow organ. Such holes are useful in surgically preparing the hollow organ or body vessel for connection with another hollow organ, body vessel or prosthetic conduit. For example, an assist device is generally connected to the left ventricle through a ventriculotomy created at the apex of the left ventricle. This ventriculotomy is most easily created with a punch or trephine. Control over such a procedure must be precise so as not to damage the ventricular wall or intracardiac structures such as papillary muscles, chordae tendinae, etc. The punch of the current invention allows for precise location and alignment of the cutting segment. The punch of the current invention also allows for precise advance of the cutting blade and a very clean cut of the tissue. Such clean cuts improve the healing when the hole in the body vessel or hollow organ is closed or attached to a connection, either prosthetic or natural.

18 Claims, 7 Drawing Sheets

US 6,863,677 B2

METHOD AND APPARATUS FOR TREPHINATING BODY VESSELS AND HOLLOW ORGAN WALLS

FIELD OF THE INVENTION

The field of this invention is surgery and especially, cardiovascular, general or peripheral vascular surgery.

BACKGROUND OF THE INVENTION

During surgical procedures such as placement of a ventricular assist device, blood vessel anastomosis, aortotomy, gastrotomy, enterotomy, or access to other hollow organs and vessels, it is useful to have a specialized tool to create a circular opening or fenestration in the wall of the vessel or organ. Punches have been developed for use in surgery that create such fenestrations. Examples of the prior art include U.S. Pat. No. 3,949,747 to Hevesy, U.S. Pat. No. 4,018,228 to Goosen, U.S. Pat. No. 4,122,855 to Tezel, U.S. Pat. No. 4,216,776 to Downie et al., U.S. Pat. No. 5,129,913 to Ruppert, U.S. Pat. No. 5,827,316 to Young et al., U.S. Pat. No. 5,910,153 to Mayenberger, and U.S. Pat. No. 5,972,014 to Nevins. More recent patents include U.S. Pat. No. 6,080,173 to Williamson IV et al., U.S. Pat. No. 6,080,176 to Young, U.S. Pat. No. 6,176,867 to Wright, and U.S. Pat. No. 6,187,022 to Alexander Jr. et al.

Problems with the current punches or coring devices occur both when the punch is positioned and actuated. With current systems, the cutting occurs by application of manual force by the surgeon. By requiring manual force to punch the hole in the organ or vessel wall without an adequate point of reference, the surgeon is not able to ascertain that the hole will be created along the correct path and at the selected location, prior to actually punching the hole. In addition, the current punches operate by means of a die without opposing back-up-plate cutting members. Examples of current punch mechanisms are similar to scissors where the cutting blade passes by an opposing brace or other cutting blade. These systems all create suboptimal openings and leave ragged tissue edges.

New devices and methods are needed which facilitate creation of a hole in the hollow organ or vessel and allow confirmation of proper location, orientation, and coring path prior to actual creation of the hole in the hollow organ or vessel wall. In addition, devices are needed to make more precise, cleaner holes in the tissue. Such cleaner holes allow for more precise surgery, more controlled placement of anastomoses, more control over surgically created geometry, reduced blood loss and resultant improved patient outcome.

SUMMARY OF THE INVENTION

This invention relates to a trephine, coring tool, or punch for creating a hole or stoma at a precise, desired location in a hollow organ or body vessel. The present invention is a cutting surface that is opposed by an anvil to create a clean cut. The anvil comprises a tapered nose to facilitate penetration into the organ or vessel once a preliminary incision has been performed. The cutting surface is spring loaded to perform the actual cutting under pre-assigned force. The system allows for location reference by allowing the punch to rest, under spring force, against the tissue to be cut while final alignment is completed, thus allowing a more accurate cut.

In the prior art previously cited U.S. Pat. No. 4,018,228 to Goosen, U.S. Pat. No. 4,216,776 to Downie et al., U.S. Pat. No. 5,129,913 to Ruppert, U.S. Pat. No. 5,827,316 to Young et al., U.S. Pat. No. 5,910,153 to Mayenberger, U.S. Pat. No. 5,972,014 to Nevins, U.S. Pat. No. 6,080,173 to Williamson IV et al., and U.S. Pat. No. 6,080176 to Young use a shearing or scissoring action between two blades to cut tissue. U.S. Pat. No. 3,949,855 to Hevesy, U.S. Pat. No. 4,122,855 to Tezel, and U.S. Pat. No. 6,187,022 to Alexander et al. use a knife or single sharpened edge with no opposing blade or surface to cut tissue. Both of these methods produce a ragged cut. The present invention distinguishes over the cited prior art because the tissue is cut between a sharp edge and an opposing, flat, anvil-like surface to produce a clean cut.

The invention is most useful in cardiac surgery to create an opening or channel for cannula access to the ventricles of the heart or blood vessels near the heart. It is also useful for vascular surgery where side-to-side or end-to-side anastomoses need to be made. Alternatively, the system allows for general tissue biopsies and other general surgical applications on hollow organs or vessels such as a tracheostomy.

DETAILED DESCRIPTION OF THE INVENTION

Figure 1A:
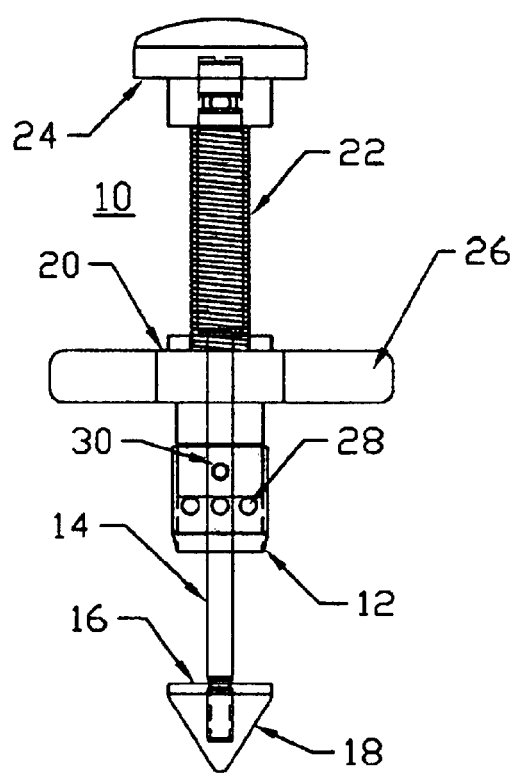
FIG. 1A illustrates a side view of the trephine, punch or coring tool of the current invention with the cutter fully retracted.

FIG. 1A illustrates a hollow organ coring tool, trephine, or punch 10 of the present invention. The coring tool 10 comprises a cutter 12, a central axially elongated shaft 14, an anvil 16, a trocar or tapered tip 18, a handle 20, a spring 22, and a knob 24. The cutter 12 comprises a plurality of holes 28. The handle 20 further comprises a plurality of wide flange-like members or wings 26. The handle 20 optionally comprises a setscrew 30. The cutter 12, the anvil 16, the trocar or tapered tip 18, the handle 20, the spring 22, and the knob 24 are disposed concentrically on the axially elongate shaft 14. The knob 24 is affixed to the proximal end of the shaft 14. The handle 20 is affixed to the cutter 12 with the optional setscrew 30. The handle 20 and attached cutter 12 slide rotationally and longitudinally in a one to one motion along and around the shaft 14. The spring 22 is slidably disposed between the knob 24 and the handle 20 and imparts a pre-determined force on the handle 20-cutter 12 assembly. The anvil 16 is affixed to the proximal end of the trocar or tip 18 and the tip 18 is affixed to the distal end of the shaft 14.

FIG. 1A shows the coring tool 10 with the cutter 12 in the fully retracted position. The cutter 12 is a cylindrical blade made from materials capable of being sharpened and with a high degree of hardness. Such materials include but are not limited to stainless steel, cobalt—nickel—chrome alloys, titanium alloys and the like. The cutter 12 has a sharpened configuration on its distal most edge to permit surgical cutting of body tissue. The distal cutting edge of the cutter 12 is, preferably, smooth but sharpened. Alternatively, the distal cutting edge may be serrated like a bread knife. The hollow interior of the cutter 12 is sufficiently long to allow the cored-out tissue to reside therein without being compressed. Holes 28 are optionally provided in the proximal end or sides of the cutter 12 to allow for fluid escape during cutting, thus preventing pressure buildup within the cutter 12. The cutter 12 may be any diameter necessary for the surgical procedure. The diameter of the cutter 12 ranges from 0.5 mm to 100 mm or even larger with the diameter range preferably being from 1 mm to 50 mm.

In another embodiment, the cutter 12 may be an electrocautery or electrocutting device consisting of an electrode. The electrode is electrically connected to a cable leading to one pole of an external electrocautery power supply. Another electrical pole of the power supply is an electrically conducting grounding pad electrically affixed to the patient's skin or other body organ, often with the aid of electrically conducting gel.

In a further embodiment, the cutter 12 may be rotationally vibrated using an electrical motor or one or more electrical actuators. Examples of electrical actuators include those fabricated from shape-memory nitinol with or without an elastic substrate. Ohmic heating of the nitinol actuators by application of electrical current causes reversible length change in said actuators. Opposably mounted actuators, energized one at a time, provide torque to rotationally vibrate the cutter 12 about the shaft 14. The actuators and cutter 12 operate at frequencies up to about 200 Hz. Electrical current is provided through an electrical cable leading to an external set of batteries and a controller. Alternatively, said controller and batteries could be mounted integral to the coring tool 10, such as in the knob 24, for example. Such rotational vibration makes the cutter 12 function like an electric bread knife with enhanced cutting capability over a stationary knife-edge.

In a preferred embodiment, the handle 20 is affixed to the cutter 12. The handle 20 provides rotational force to the cutter 12 to assist in tissue penetration. The optional setscrew 30 may be used to attach the handle 20 to the cutter 12. Other ways to attach the handle 20 to the cutter 12 are the use of a rolled-pin, adhesives or over-molding. Mechanical advantage for manual rotation is derived from the wide flange like members or wings 26 on the handle 20 that allow increased moment arm to be applied to the handle 20 by the fingers of the surgeon. The handle 20 is preferably made from polymers such as but not limited to polycarbonate, acetal copolymers, acrylinitrile butadiene styrene, polyvinyl chloride and the like. The handle 20 optionally is provided with holes or openings that communicate with the optional holes 28 in the cutter 12 to allow for air and fluid escape from the interior of the cutter 12 through the handle 20 to the external environment during the coring process.

Optionally, the handle 20 comprises a latch or lock to maintain its position on shaft 14 in the retracted position under force of the spring 22. To move the handle 20 distally, the optional lock is released allowing the handle 20 to be advanced along the shaft 14 toward the anvil 16. The handle 20 further optionally comprises a damper or shock absorber to prevent the high velocity accidental release of the handle 20 and cutter 12 into the tissue.

Figure 6A:
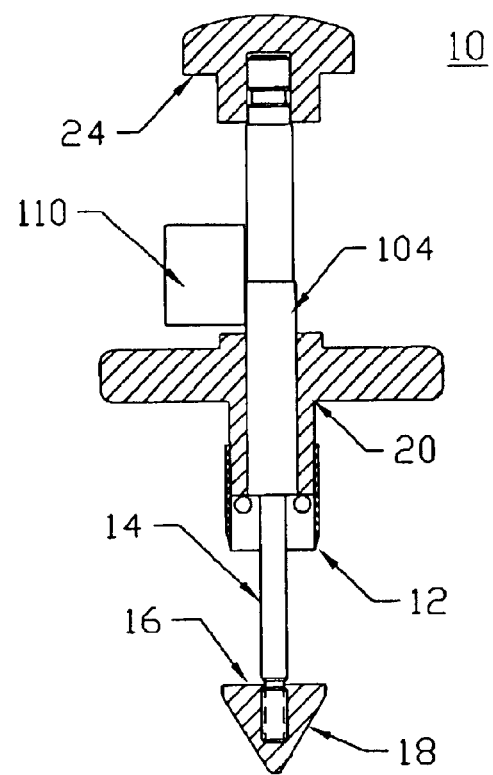
FIG. 6A illustrates a longitudinal cross-sectional view of the trephine, punch or coring tool comprising a jackscrew to replace the function of the spring.
Figure 6B:
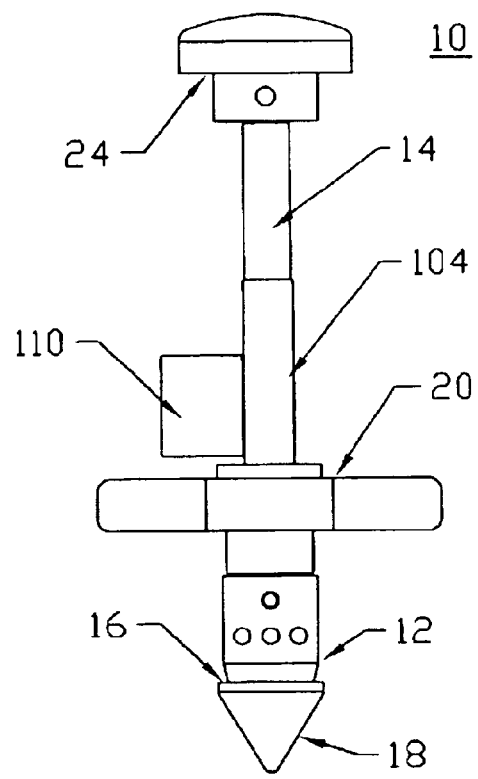
FIG. 6B illustrates a side view of the trephine, punch or coring tool comprising the jackscrew, wherein the cutter has been advanced against the anvil.

Alternatively, as illustrated in FIGS. 6A and 6B, the handle 20 may be rotated by a motor or gear motor 110 which is electrically powered by a battery disposed either external to or internal to the punch 10. External battery power is delivered to the motor 110 through a cable with a plurality of conductors. On and off operation of the motor 110 is controlled through a switch on the punch knob 24 or the handle 20, by a foot switch, or by a sound activated switch.

Figure 1B:
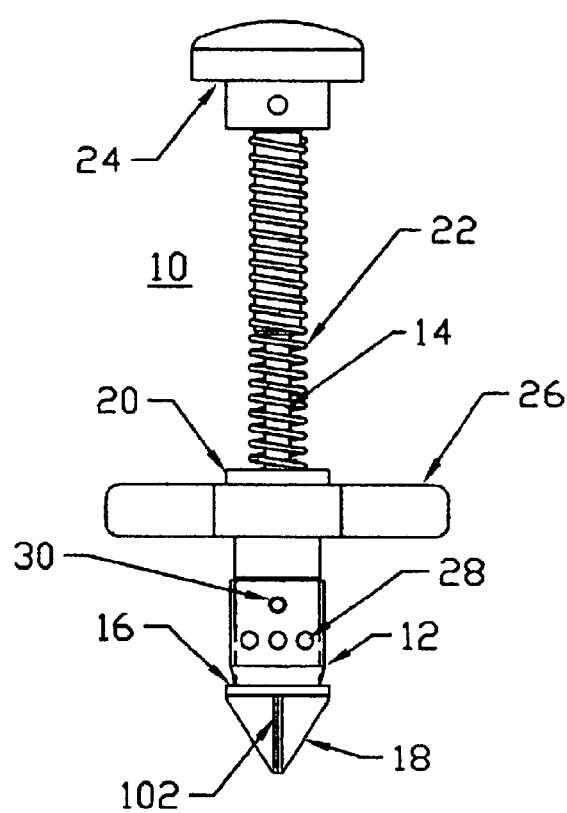
FIG. 1B illustrates a side view of the trephine, punch or coring tool of the current invention with the cutter fully advanced against the anvil.

FIG. 1B shows the handle 20-cutter 12 assembly fully advanced against the anvil 16. The spring 22 is disposed between the knob 24 and the handle 20 and applies the desired force to the handle 20-cutter 12 assembly distally toward the anvil 16 with a pre-determined force. The pre-determined force is between 0.10 and 25 pounds and, preferably, between 1 and 10 pounds. This force is advantageous in performing a controlled tissue excision. The spring 22 also allows the cutter 12 to be disposed against the tissue prior to actual excision, without cutting, so that correct alignment may be determined by the surgeon. The spring 22 is, preferably, made from spring hardened metals such as stainless steel 304, stainless steel 316, nitinol, titanium alloys and the like. The spring 22 ensures that a seal is maintained between the cutter 12 and the tissue so that hemostasis is maximized or leakage of body fluids is minimized.

In another embodiment, as illustrated in FIGS. 6A and 6B, the function of the spring 22 is replaced by a threaded jackscrew assembly 104. The shaft 14 is threaded and engages mating threads on the handle 20. By rotating the handle 20, the cutter 12 is rotated and simultaneously advanced proximally or distally in a positive displacement fashion. FIG. 6A shows the coring tool 10 with the cutter 12 retracted away from the anvil 16. FIG. 6B shows the coring tool 10 with the cutter 12 advanced against the anvil 16.

Figure 7A:
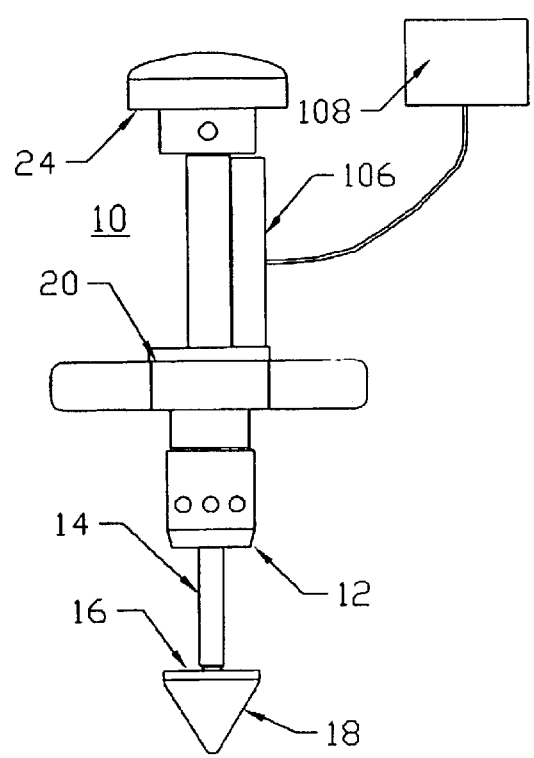
FIG. 7A illustrates a side view of the trephine, punch or coring tool comprising a hydraulic cylinder to replace the function of the spring.
Figure 7B:
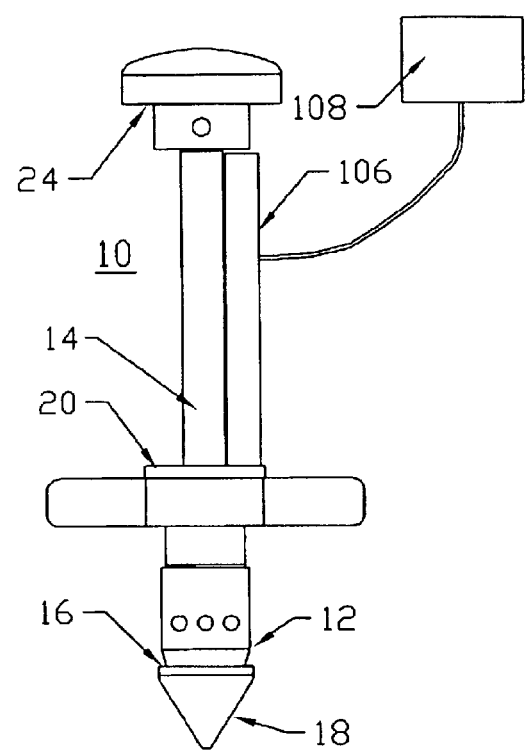
FIG. 7B illustrates a side view of the trephine, punch or coring tool comprising the hydraulic cylinder, wherein the cutter has been advanced against the anvil.

In yet another embodiment, as illustrated in FIGS. 7A and 7B, the function of the spring 22 is replaced by a hydraulic cylinder 106 and hydraulic pressure source 108 with a valve or switch to control pressure into said cylinder 106. FIG. 7A shows the coring tool 10 with the cutter 12 retracted away from the anvil 16. FIG. 7B shows the coring tool 10 with the cutter 12 advanced against the anvil 16.

The central shaft 14 maintains axial and longitudinal orientation of the punch 10 components. The shaft 14 is preferably fabricated from metals such as stainless steel, cobalt—nickel—chrome alloys, titanium alloys and the like. The shaft 14 may also be fabricated from hardened polymers such as glass-filled polycarbonate and the like. Holes or circumferential depressions in the shaft 14 permit attachment of components using setscrews or over-molding techniques. The shaft 14 geometry allows for expeditious replacement of optionally disposable components such as the cutter 12, anvil 16 and tip 18. The central shaft 14, optionally, comprises one or more circumferential alignment marks to confirm the cutter 12 position from the proximal end of the punch 10.

The tapered tip 18 is affixed to the distal end of the shaft 14 in a stationary manner. Fixation of the tip 18 to the shaft 14 is accomplished by over-molding, a setscrew or by internal threads on the trocar or tapered tip 18 engaging male threads on the shaft 14. The trocar or tapered tip 18 has a conical configuration and allows penetration of the hollow organ or vessel by the entire tip 18 anvil 16 assembly following an initial incision with a sharp surgical instrument. The distal end of the trocar 18 may be either sharp or rounded. Use of the sharp end on the trocar 18 permits use of the coring tool 10 without first making a separate surgical incision in the tissue. Longitudinal edges or ridges 102 are optionally disposed on the conical surface of trocar or tip 18 to enhance tissue penetration. Alternatively, the tip 18 may be oscillated or vibrated with an electrical actuator or motor to facilitate penetration into the tissue. The oscillation is useful for either blunt dissection or sharp dissection of the tissue.

The anvil 16 is a flat surface disposed distally to the cutter 12 and aligned in a plane generally perpendicular to the axis of the shaft 14. The anvil 16 is at least as wide as the largest exterior cutting dimension of the cutter 12. In this way, the anvil 16 serves to positively stop the cutter 12. The cutter 12 is advanced against the anvil 16 during the cutting procedure. The cutter 12 does not pass beyond the proximal surface of the anvil 16. In its lowest energy or inactive state, the cutter 12 rests against the anvil 16 with a net compressive force and the spring 22 expanded to its maximum allowable amount. The compressive force between the closed cutter 12 and the anvil 16 serves to maintain contact between the surfaces and promote cutting at the end of the stroke.

The anvil 16 and the tapered tip 18 are, preferably fabricated from the same piece of material for economy and ease of fabrication. Alternatively, the anvil 16 and the tapered tip 18 may be separate components and may be longitudinally disconnected or they may be longitudinally connected. Both the anvil 16 and the trocar or tapered tip 18 are radially constrained by the shaft 14. The anvil 16 is attached to shaft 14 by a setscrew, internal threads for engagement with male threads on the shaft 14, adhesive bonding or over-molding. The anvil 16 and the trocar or tapered tip 18 are, preferably, fabricated from polymeric materials such as but not limited to polyvinyl chloride, acetal copolymers, polycarbonate, acrylinitrile butadiene styrene and the like. They may alternatively be fabricated from metals such as stainless steel, cobalt—chrome—nickel alloys, titanium alloys and the like.

The anvil 16 optionally comprises pre-placed attachment devices, such as staples, sutures or posts that remain in the tissue around the coring site to facilitate subsequent placement of anastomotic devices.

The knob 24 terminates the proximal end of the shaft 14 and allows for positioning of the punch 10 by the surgeon. The knob 24 is blunt and preferably is fabricated from the same materials as the trocar or tip 18 or the anvil 16. The knob 24 is affixed to the shaft 14 with setscrews, adhesives, or over-molding or the knob 24 is affixed by female threads that engage male threads on the shaft 14.

Figure 2:
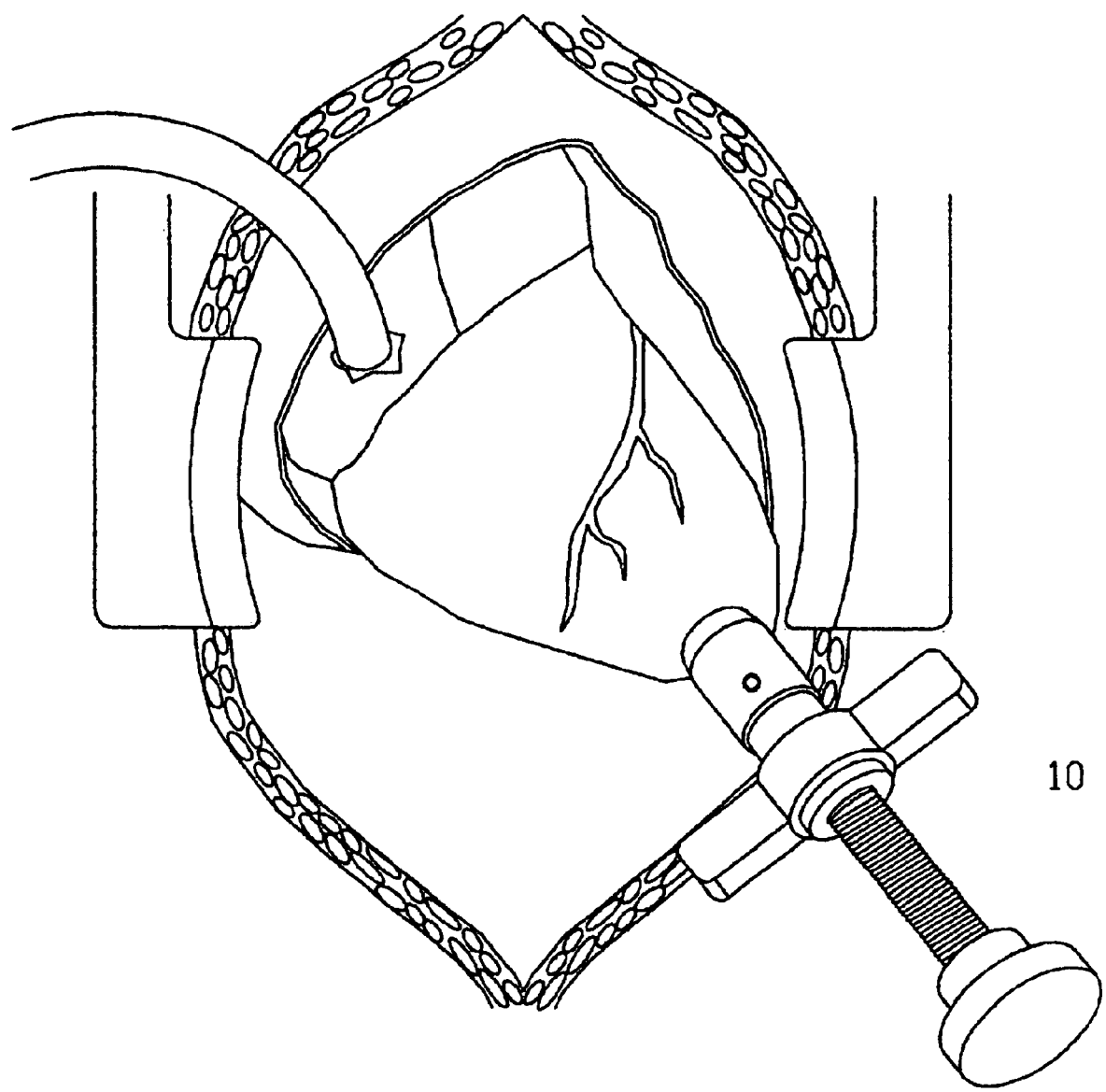
FIG. 2 illustrates the trephine, punch or coring tool applied to the apex of the ventricle of the heart prior to advancing the cuffing blade.
Figure 3:
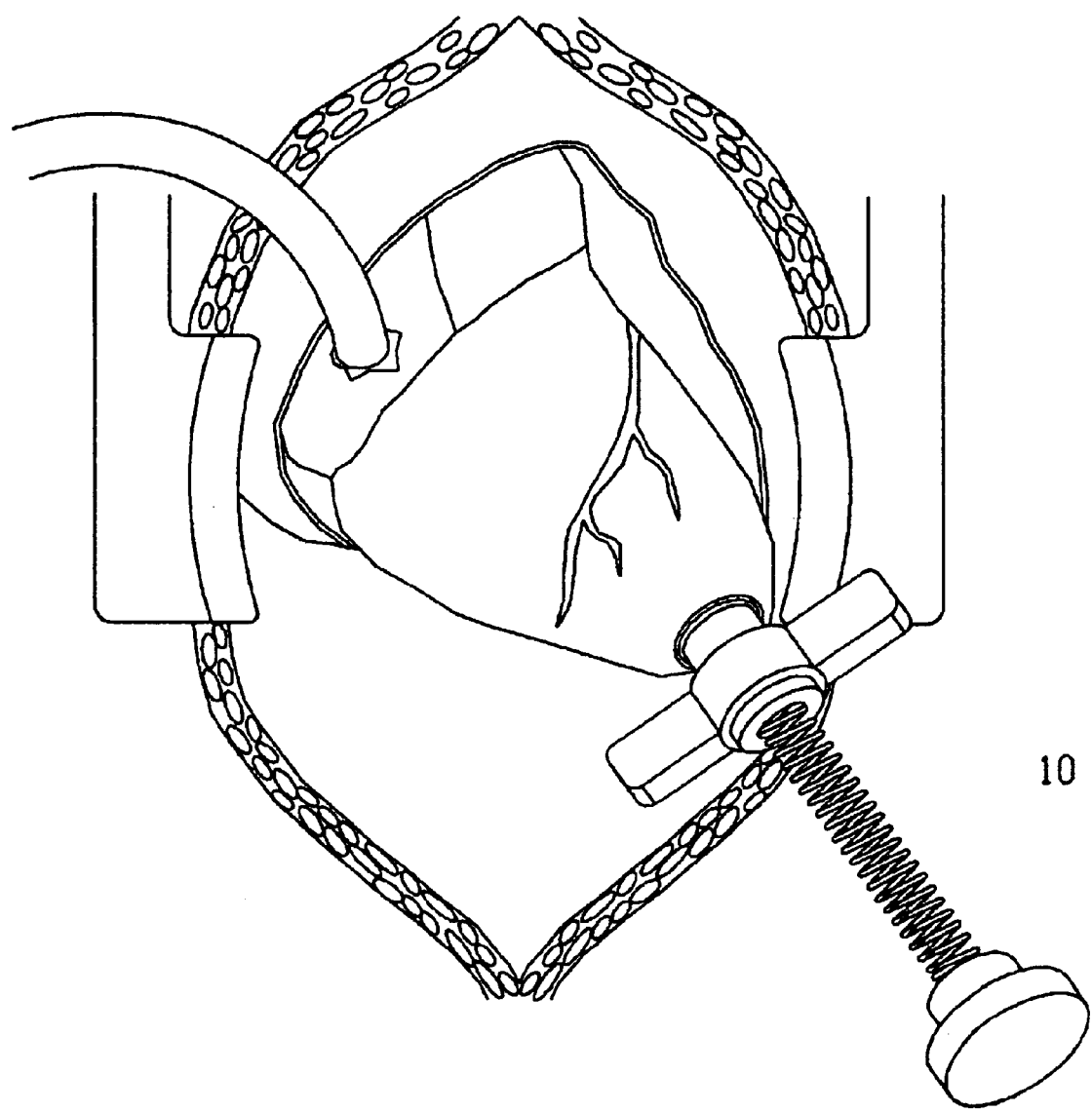
FIG. 3 illustrates the trephine, punch or coring tool after the blade has been advanced through the apex of the ventricular wall of the heart.
Figure 4:
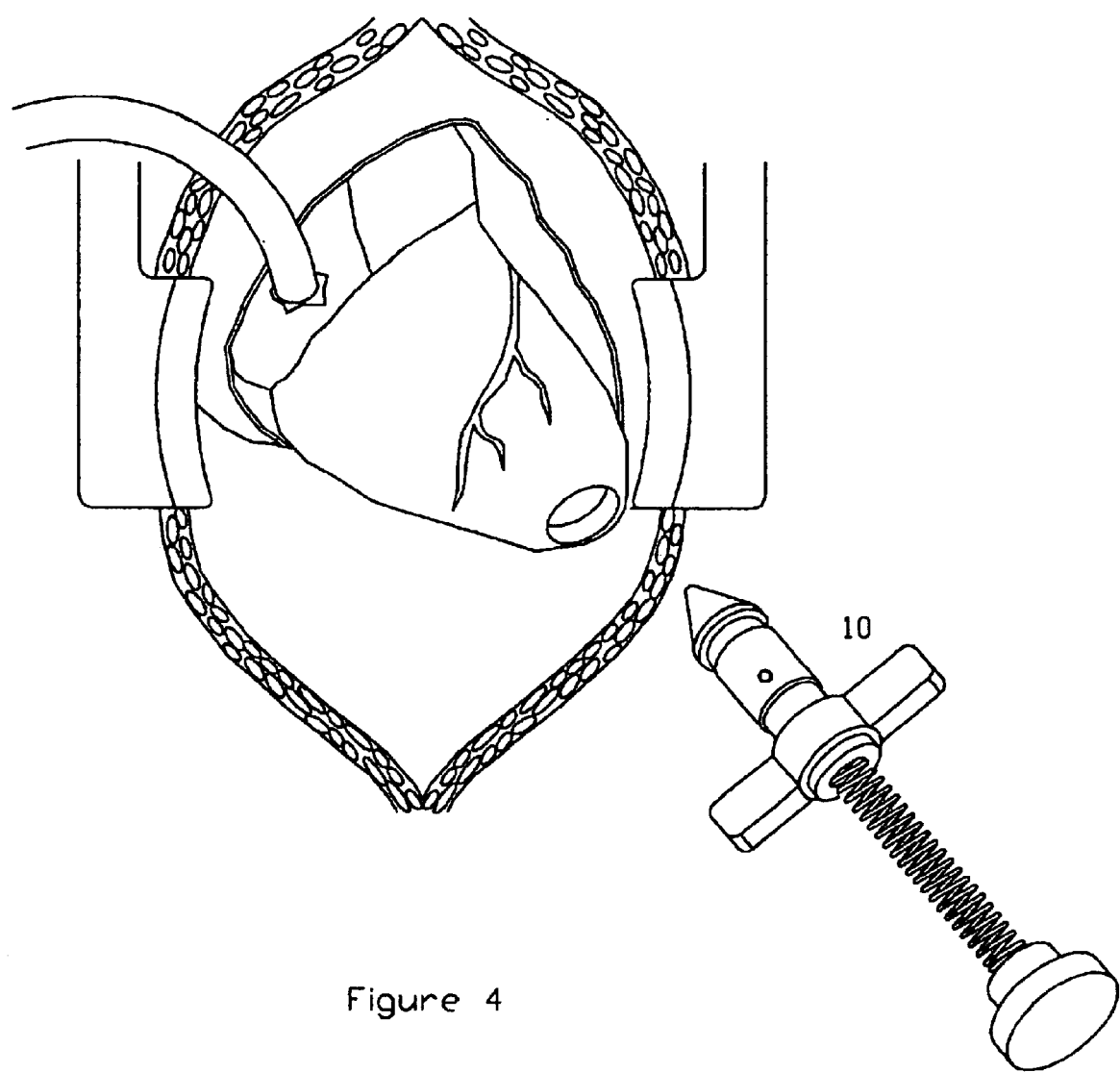
FIG. 4 illustrates the ventricular wall after removal of the trephine, punch or coring tool and the excised tissue.

Referring to FIGS. 2, 3, and 4, the procedure for hollow organ coring or trephination is accomplished by first creating a small incision at the desired penetration location using a sharp surgical instrument such as a scalpel. The cutter 12 is retracted by manually withdrawing the handle 20 wings 26 proximally toward the knob 24. The spring 22 is compressed when retracting the handle 20 and cutter 12. The tapered tip 18 and anvil 16 assembly is advanced into the incision until the anvil 16 has passed beyond the interior surface of the hollow organ or vessel. The handle 20 is next released and the cutter 12 is positioned against the exterior of the hollow organ as shown in FIG. 2. Once position has been confirmed or adjusted, the handle 20 is manually rotated to initiate cutting of the tissue by the cylindrical cutter 12. As shown in FIG. 3, the handle 20 and cutter 12 are rotated until full penetration of the hollow organ has occurred, under force of the spring 22, and the distal edge of the cutter 12 rests against the anvil 16.

Complete penetration and cutter 12 to anvil 16 contact may be confirmed by placement of a plurality of alignment marks on the shaft 14. The alignment marks become visible once the cutter 12 and handle 20 have been advanced sufficiently. The punch 10 is next withdrawn proximally, removing the cored-out piece of tissue from the organ as shown in FIG. 4. Prevention of hemorrhage or fluid leakage from the hollow organ or vessel is accomplished by manual compression or placement of a temporary plug. This device and procedure are especially useful when performing coring on the beating heart.

Typically, the surgeon manually cores the patient's hollow organ or vessel using the punch or coring tool 10. The coring tool 10 could, alternatively, be held and manipulated by a robotic arm or laparoscopic instrument.

Figure 5A:
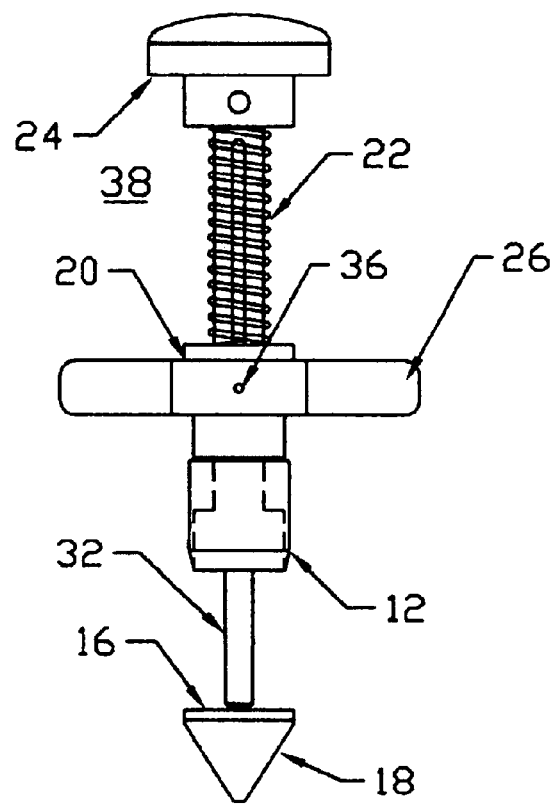
FIG. 5A illustrates another embodiment of a side view of the trephine, punch or coring tool with the anvil fully advanced.
Figure 5B:
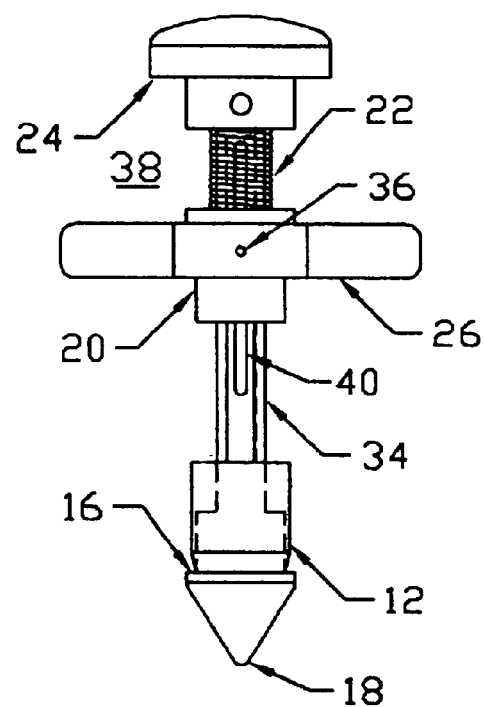
FIG. 5B illustrates a side view of the trephine, punch or coring tool with the anvil fully retracted against the cutter.

FIGS. 5A and 5B illustrate another embodiment of a hollow organ coring tool, trephine, or punch 38. The coring tool 38 comprises the cutter 12, the anvil 16, the trocar or tapered tip 18, the handle 20, the spring 22, and the knob 24. The coring tool 38 also comprises an inner shaft 32, an outer shaft 34, a pin 36, and an axial slot 40. The handle 20 further comprises the plurality of wide flange-like members or wings 26.

The cutter 12, the handle 20, the spring 22, and the knob 24 are disposed concentrically on the axially elongate outer shaft 34. The anvil 16 and the trocar or tip 18 are disposed concentrically on the axially elongate inner shaft 32. The inner shaft 32 is slidably disposed inside the outer shaft 34 and the inner shaft 32 extends beyond the outer shaft 34 at least the thickness of the vessel or organ to be cored.

The handle 20 is not affixed to the cutter 12. Instead, the handle 20 is affixed to the inner shaft 32 by the pin 36 through the axial slot 40 in the outer shaft 34. The cutter 12 is affixed to the distal end of the outer shaft 34. The handle 20, which is affixed to the inner shaft 32, sets above the cutter 12, which is affixed to the outer shaft 34.

The knob 24 is affixed to the proximal end of the outer shaft 34. The anvil 16 is affixed to the proximal end of the trocar or tip 18 and the tip 18 is affixed to the distal end of the inner shaft 32.

The spring 22 sets around the outer shaft 34, between the knob 24 and the handle 20. The spring 22 forces the tip 18 and anvil 16 distally away from the cutter 12. Manual retraction of the handle 20 proximally causes proximal retraction of the anvil 16 toward the cutter 12. The spring 22 becomes increasingly compressed as the handle 20 is moved proximally toward the knob 24.

Referring to FIG. 5A, the handle 20, the tip 18, the anvil 16, and inner shaft 32 of the trephine 38 are fully advanced. The spring 22 is not compressed and is in its lowest energy position. The pin 36 rests in the distal end of the slot 40 and prevents the handle 20, the tip 18 and the anvil 16 from advancing further.

The handle 20 or the knob 24 optionally comprise a lock that is manually operated and selectively prevents movement of the inner shaft 32 relative to the outer shaft 34.

Referring to FIG. 5B, the handle 20, the tip 18, the anvil 16, and the inner shaft 32 are fully retracted. The spring 22 is fully compressed and in its highest energy position. Retraction of the handle 20 is accomplished with one hand over the knob 24 and fingers wrapped around the wings 26 in the handle 20. Pulling the fingers toward the knob 24 causes the anvil 16 to move proximally toward the cutter 12. The movement stops when the anvil 16 meets the cutter 12.

The procedure for hollow organ coring or trephination is accomplished by first creating a small incision at the desired penetration location using a sharp surgical instrument such as a scalpel. The tapered tip 18 and anvil 16 assembly is advanced into the incision until the anvil 16 has passed beyond the interior surface of the hollow organ or vessel and the cutter 12 rests on the exterior of the hollow organ or vessel. Once position has been confirmed or adjusted, the handle 20 is pulled toward the knob 24 to initiate cutting of the tissue by the circular cutter 12. The handle 20 is pulled until the distal edge of the cutter 12 rests against the anvil 16 and the organ has been cored. Complete penetration and cutter 12 to anvil 16 contact may be confirmed by placement of a plurality of alignment marks on the outer shaft 34. The alignment marks become visible once the anvil 16 and the handle 20 have been retracted sufficiently. The punch 38 is next withdrawn proximally, removing the cored-out piece of tissue from the organ.

The hollow organ coring tool, trephine, or punch 38 is fabricated from the same materials as the hollow organ coring tool, trephine, or punch 10 and comprises the same or similar options as the hollow organ coring tool, trephine, or punch 10. For example, the cutter 12 of the punch 38 may be rotated by a motor or actuator to facilitate tissue penetration.

The present invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

I claim:

1. An apparatus adapted for cutting holes in a body vessel or hollow organ comprising:
    a shaft, wherein the shaft has a longitudinal axis;
    a cutting blade;
    a controlled force to advance the cutting blade along the longitudinal axis of the shaft; and
    an anvil having a surface against which the cutting blade is advanced, wherein the surface of the anvil is perpendicular to the longitudinal axis of the shaft, wherein the anvil is at least as wide as a largest exterior diameter of the cutting blade, and wherein the cutting blade does not pass beyond the surface of the anvil;
    wherein the cutting blade rotates relative to the anvil while the cutting blade is being advanced toward the anvil.

2. The apparatus of claim 1 wherein said controlled force on the cutting blade is generated by a spring with a predetermined or selected spring constant.

3. The apparatus of claim 1 wherein said controlled force on the cutting blade is generated by a jackscrew with a knob for manual advance of said cutting blade.

4. The apparatus of claim 1 wherein said controlled force on the cutting blade is generated by a hydraulic cylinder and hydraulic pressure supply.

5. The apparatus of claim 1 wherein said controlled force on the cutting blade is generated by a jackscrew and an electric motor to advance the blade.

6. The apparatus of claim 1 wherein said anvil is fabricated from a polymeric material.

7. The apparatus of claim 1 wherein said apparatus comprises a tapered tip or trocar to promote tissue penetration.

8. The apparatus of claim 7 wherein said tapered tip or trocar includes axially disposed ridges to assist with tissue penetration.

9. The apparatus of claim 8 herein said axially disposed ridges are sharp enough to cut tissue.

10. The apparatus of claim 8 wherein said axially disposed ridges are blunted.

11. The apparatus of claim 7 wherein said anvil and said tapered tip or trocar are fabricated from the same piece of material.

12. A method for creating a hole in a hollow organ or body vessel comprising the steps of:
    creating an incision in said hollow organ or body vessel with a sharp object;
    advancing a tapered trocar through said hollow organ or body vessel at the incision site until the trocar point has completely penetrated said hollow organ or body vessel;

locating a cutting blade having a longitudinal axis coaxially disposed about said trocar so that said cutting blade is positioned correctly;

advancing said cutting blade into said hollow organ or body vessel under controlled force until said cutting blade fully rests against a blunt surface of an anvil whose outside diameter is greater than or equal to an outer diameter of said cutting blade, wherein the blunt surface of the anvil is perpendicular to the longitudinal axis of the cutting blade, and wherein a leading edge of the cutting blade does not pass beyond the blunt surface of the anvil;

rotating the cutting blade while said cutting blade is being advanced toward said anvil; and removing said cutting blade and excised tissue from the hollow organ or body vessel.

13. A punch adapted for creating holes in a body organ or vessel comprising:

a shaft with a proximal end and a distal end;

a knob affixed at or near the proximal end of the shaft;

an anvil affixed at or near the distal end of the shaft, the anvil having a proximal surface which faces the cutter and a distal surface which faces away from the cutter;

a cutter slidably disposed between said knob and said anvil, wherein the outer diameter of said cutter is less than the outer diameter of said anvil;

a controlled force to bias the cutter toward said anvil; and a mechanism to rotate said cutter, wherein the cutter rotates relative to the anvil while the cutter is being advanced toward the anvil, wherein the cutter is advanced against, but not beyond, the proximal surface of the anvil.

14. The punch of claim 13 further comprising holes in the cutter, wherein said holds vent trapped air.

15. The method of claim 12 further comprising the step of providing holes in the cutter to vent air trapped within said cutter.

16. The punch of claim 13 wherein the controlled force biases the anvil toward the cutter.

17. The punch of claim 16 wherein the controlled force is generated by a jackscrew to move the anvil against the cutter.

18. The punch of claim 16 wherein the controlled force is generated by a spring biased to move the anvil against the cutter.

* * * * *